United States Patent

Takaki et al.

[11] Patent Number: 5,677,328
[45] Date of Patent: Oct. 14, 1997

[54] ETHYLAMINO CARBAZOLE MELATONERGIC AGENTS

[75] Inventors: Katherine S. Takaki, Middletown; Marc A. Bruce, Wallingford; Graham S. Poindexter, Old Saybrook, all of Conn.; Brett T. Watson, Vaerloese, Denmark; Joseph P. Yevich, Southington, Conn.

[73] Assignee: Bristol-Myers Squibb Company, Princeton, N.J.

[21] Appl. No.: 741,485

[22] Filed: Oct. 30, 1996

Related U.S. Application Data

[60] Provisional application No. 60/008,154, Oct. 31, 1995.
[51] Int. Cl.[6] .................. A61K 31/40; C07D 209/88
[52] U.S. Cl. ................................... 514/411; 548/444
[58] Field of Search ........................... 548/444; 514/411

[56] References Cited

U.S. PATENT DOCUMENTS 3,975,398  8/1976  Werner et al. .................. 548/444
5,206,377  4/1993  McAfee .

FOREIGN PATENT DOCUMENTS

WO 9407487  4/1994  WIPO .

OTHER PUBLICATIONS

Ebisawa, et al., "Expression Cloning of a High-Affinity Melatonin Receptor From Xenopus Dermal Melanophores" *Proc. Natl. Acad. Sci.* 91: pp. 6133–6137.

Cassone, et al., "Dose-Dependent Entrainment of Rat Circadian Rhythms by Daily Injection of Melatonin" *J. Biol. Rhythms 1:* pp.219–229 (1986).

Arendt, et al., "Alleviation of Jet Lag by Melatonin: Preliminary Results of Controlled Double Blind Trail" *Br. Med. J.* 292: 1170 (1986).

Stamm, et al., "Amidoethylierung des Fluorens mit N-Acylaziridinen. Umlagerung eines N-Acylaziridins zu einem 2-Pyrrolidon" *Chem. Ber.* 111: pp. 2665–2666 (1978).

*Primary Examiner*—Robert W. Ramsuer
*Attorney, Agent, or Firm*—Aldo A. Algieri

[57]  ABSTRACT

Novel substituted carbazole compounds of Formula I are active as melatonergic agents:

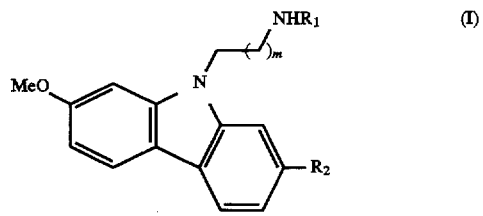

wherein:

$R_1$ is $C(O)R_3$ or $SO_2R_4$;
$R_2$ is H or $C_{1-6}$ alkoxy;
$R_3$ is $C_{1-6}$ alkyl, $(CH_2)_n SR_4$, $(CH_2)_n OR_4$, $(CH_2)_n SO_2 R_4$, or $NHR_4$;
$R_4$ is $C_{1-4}$ alkyl; and
m is 1 or 2; and
n is 1 to 4.

10 Claims, No Drawings

ETHYLAMINO CARBAZOLE MELATONERGIC AGENTS

This application claims the benefit of U.S. Provisional Application No. 60/008,154 filed Oct. 31, 1995.

BACKGROUND OF THE INVENTION

This application discloses novel carbazole compounds having aminoethyl substituents. It also concerns the preparation of these compounds, their formulations and method of use. The compounds have melatonergic properties that should make them useful in treating sleep disorders.

Melatonin (N-acetyl-5-methoxytryptamine) is a hormone synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Recent evidence demonstrates that melatonin exerts its biological effects through specific receptors. Use of the biologically active, radiolabelled agonist $[^{125}I]$-2-iodomelatonin has led to the identification of high affinity melatonin receptors in the central nervous systems of a variety of species. The sequence of one such high affinity melatonin receptor, cloned from frog dermal melanophores, has been reported (Ebisawa, et al., Proc. Natl. Acad. Sci. 91: 6133–6137, 1994). In mammalian brain, autoradiographic studies have localized the distribution of melatonin receptors to a few specific structures. Although there are significant differences in melatonin receptor distribution even between closely related species, in general the highest binding site density occurs in discrete nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., J. Biol. Rhythms, 1: 219–229, 1986). In humans, administration of melatonin has been used to treat jet-lag related sleep disturbances, considered to be caused by desynchronization of circadian rhythms (Arendt, et al., Br. Med. J. 292: 1170, 1986). Further, the use of a single dose of melatonin to induce sleep in humans has been claimed by Wurtman in International Patent Application WO 94/07487.

Melatonin binding sites have been found in several diverse tissues of the body—i.e., in the retina, suprachiasmatic nucleus, spleen, etc. Thus, melatonin exerts multiple physiological effects, is not highly selective, and its potential for producing side effects is significant. Melatonin agonists should be more selective than melatonin and give fewer side effects.

In addition, melatonin's metabolic profile can be problematic in that the compound degrades rapidly in vivo and its oral bioavailability is often low and variable. Suitable melatonin agonists could overcome these drawbacks, resulting in products having more predictable activity.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, immune disorders, and neuroendocrine disorders.

U.S. Pat. No. 5,206,377 to McAfee discloses compounds having melatonin antagonist activity which conform to formula 1:

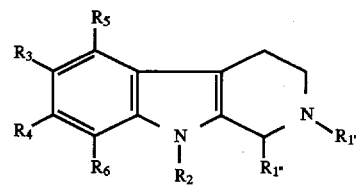

wherein $R_{1'}$ is $C_{1-6}$ alkanoyl; $R_{1''}$ is hydrogen, $C_{1-6}$ alkyl or optimally substituted phenyl; $R_2$ is hydrogen or phenyl substituted $C_{1-6}$ alkylene; and $R_3$, $R_4$, $R_5$ and $R_6$ are $C_{1-6}$ alkyl, $C_{1-6}$ alkoxy or optionally substituted phenoxy. The McAfee compounds, which are not agonists as desired, do not contain N-amidoethyl substituents.

Stamm, et al., at Chem. Ber., 111:pp. 2665–6 (1978), show the amidoethylation of fluorene with N-acyl-aziridines to yield compounds of formula 2:

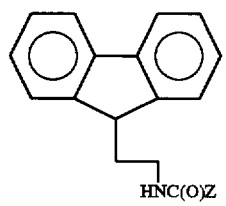

wherein Z is part of a carbamate, urea or amide group.

SUMMARY AND DETAILED DESCRIPTION OF THE INVENTION

SUMMARY OF THE INVENTION

The invention is concerned with substituted carbazoles of Formula I, salts thereof, and compositions and methods which employ them.

Formula I is:

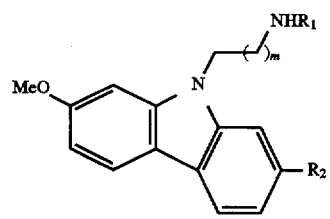

wherein:

$R_1$ is $C(O)R_3$, $C(S)R_3$, or $SO_2R_4$;

$R_2$ is H or $C_{1-6}$ alkoxy;

$R_3$ is $C_{1-6}$ alkyl, $(CH_2)_nSR_4$, $(CH_2)_{n4}$, $(CH_2)_nSO_2R_4$, or $NHR_4$;

$R_4$ is $C_{1-4}$ alkyl; and m is 1 or 2; and n is 1 to 4.

The melatonergic agents of the invention have several advantages over similar agents. They are active in tests which demonstrate human $ML_1$, i.e., $ML_{1a}$ or $ML_{1b}$, receptor binding. Many of the compounds have $IC_{50}$ binding values of 500 nM or less.

Furthermore, the instant compounds have been demonstrated to be agonists as determined by their melatonin-like ability to block the forskolin-stimulated accumulation of cyclic AMP in certain cells.

Also, selected compounds have been tested and found to be active in the "clock in the dish" test, an indicator of a compound's effectiveness in moderating circadian rhythms.

These and other advantages will become more apparent after consideration of the specification and claims.

DETAILED DESCRIPTION

The new melatonergic agents described herein conform to formula I:

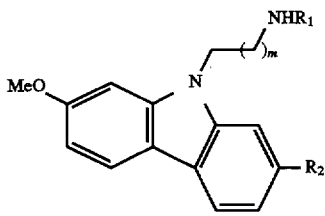

wherein:

$R_1$ is $C(O)R_3$, $C(S)R_3$, or $SO_2R_4$;

$R_2$ is H or $C_{1-6}$ alkoxy;

$R_3$ is $C_{1-6}$ alkyl, $(CH_2)_nSR_4$, $(CH_2)_nOR_4$, $(CH_2)_nSO_2R_4$, or $NHR_4$;

$R_4$ is $C_{1-4}$ alkyl; and m is 1 or 2; and n is 1 to 4.

By "alkyl", is meant branched, straight chain or cyclic alkanyl groups having the number of carbon atoms indicated. Cycloalkyl groups contain from 3 to 6 carbons.

By "alkoxy" is meant alkanyloxy groups having branched or straight chains. $R_2$ groups contain 1 to 6 carbon atoms.

m can be 1 or 2.

n is 1 to 4, preferably 1.

One preferred group of Formula I compounds include those wherein $R_2$ is hydrogen or a methoxy group m is 1 and n is 1. In this group, compounds wherein $R_1$ is C(O)alkyl, C(O)cycloalkyl, C(S)NHalkyl, C(O)CH$_2$Salkyl, or C(O) NHalkyl are highly preferred.

Some compounds in this first preferred group are:

N-[2-(2-Methoxy-9H-carbazol-9-yl)ethyl]butanamide;

N-[2-(2-Methoxy-9H-carbazol-9-yl)ethyl] cyclopropanecarboxamide;

N-[2-(2,7-Dimethoxy-9H-carbazol-9-yl)ethyl] butanamide;

N-[2-(2,7-Dimethoxy-9H-carbazol-9-yl)ethyl]-2-methylpropanamide;

N-[2-(2,7-Dimethoxy-9H-carbazol-9-yl)ethyl] cyclopropanecarboxamide;

N-[2-(2,7-Dimethoxy-9H-carbazol-9-yl)ethyl] methylthioacetamide;

N-[2-(2,7-Dimethoxy-9H-carbazol-9-yl)ethyl]-N'-methylurea; and

N-Ethyl-N'-[2-(2,7-dimethoxy-9H-carbazol-9-yl)ethyl] urea.

Another preferred group of compounds include those wherein $R_2$ is methoxy, m is 2 and n is 1. Among these, compounds wherein $R_1$ is C(O)alkyl or C(O)cycloalkyl are highly preferred.

Some compounds of this second preferred group are:

N-[3-(2,7-Dimethoxy-9H-carbazol-9-yl)propyl] acetamide;

N-[3-(2,7-Dimethoxy-9H-carbazol-9-yl)propyl] propanamide;

N-[3-(2,7-Dimethoxy-9H-carbazol-9-yl)propyl] butanamide;

N-[3-(2,7-Dimethoxy-9H-carbazol-9-yl)propyl]-2-methylpropanamide; and

N-[3-(2,7-Dimethoxy-9H-carbazol-9-yl)propyl] cyclopropanecarboxamide.

Preferred compounds have IC$_{50}$ values of 250 nM or less in human ML$_{1a}$ binding tests.

Compounds of formula I also encompass solvates, particularly hydrates thereof. In general, any non-toxic pharmaceutically acceptable solvate of a formula I compound can be used in a quantity suitable to yield melatonergic effects.

The invention also encompasses geometric and optical isomers which arise as a consequence of structural asymmetry. Separation of individual isomers is accomplished by the application of various methods known to practioners in the art.

The compounds of the invention are made using one or more of the following techniques:

SYNTHETIC ROUTE AND PROCEDURES

The compounds described herein can be made via the following synthetic schemes and methods:

Scheme 1

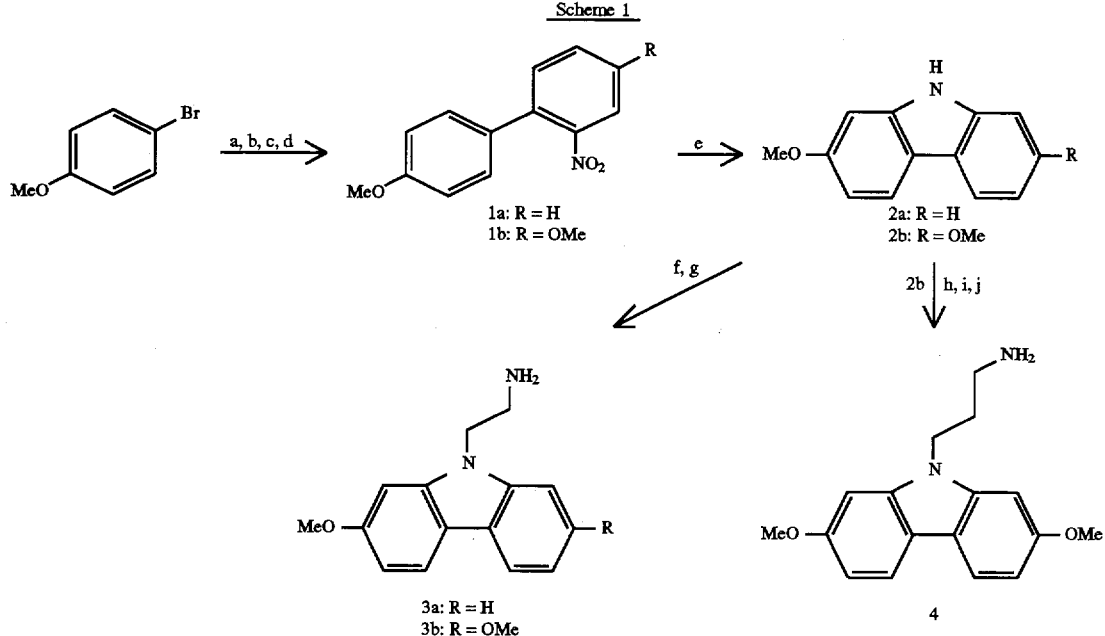

a: Mg, I$_2$, THF, Δ.
b: B(OMe)$_3$, THF.
c: 5% H$_2$SO$_4$.

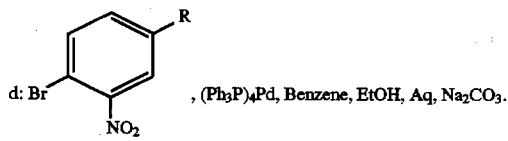, (Ph$_3$P)$_4$Pd, Benzene, EtOH, Aq, Na$_2$CO$_3$.

e: P(OEt)$_3$, Δ.
f: NaH, bromoacetonitrile, DMF.
g: H$_2$, NH$_3$, Raney Ni, 2-methoxyethanol.
h: NaH, acrylonitrile, DMF.
i: H$_2$, Raney Ni, Ac$_2$O.
j: 20% NaOH, EtOH, Δ.

Intermediate 9H-Carbazole-9-akylamines 3 and 4 (Scheme 1). Both starting biphenyl derivatives 1a and 1b were synthesized by Suzuki coupling methodology [Martin, et al, *Acta Chem. Scand.* 47, 221–230 (1993); and Miyaura, et al, *Syn. Commun.*, 11, 513 (1981)]. A Grignard reagent was prepared from 4-bromoanisole which was subsequently reacted with trimethyl borate in THF. Hydrolysis of the product in aqueous H$_2$SO$_4$ gave 4-methoxyphenylboronic acid. This was then coupled to 1-bromo-2-nitrobenzene or 4-bromo-3-nitroanisole in a mixture of (Ph$_3$P)$_4$Pd, aqueous Na$_2$CO$_3$, EtOH, and benzene to give 1a or 1b, respectively. The biphenyls 1a and 1b were subsequently refluxed in triethyl phosphite to give the carbazoles 2a and 2b. These were then alkylated with bromoacetonitrile in NaH/DMF to afford the respective carbazole-9-acetonitriles. The reduction of the nitriles was accomplished with Raney nickel and aqueous ammonia in 2-methoxyethanol to give the 9H-carbazole-9-ethanamines 3a and 3b. The propanamine 4 was prepared by conjugate addition of 2b to acrylonitrile in NaH/DMF, followed by reduction of the resulting propionitrile with Raney nickel in Ac$_2$O to yield the propyl acetamide. Subsequent hydrolysis in 20% NaOH and EtOH gave the 9H-carbazole-9-propanamine 4.

Scheme 2

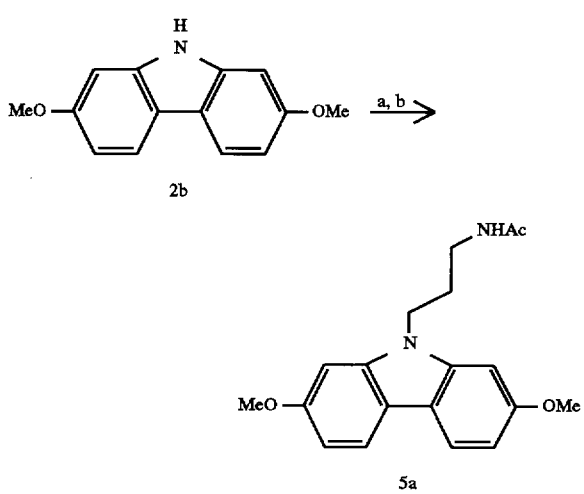

a: acrylonitrile, NaH, DMF.
b: H$_2$, Raney Ni, Ac$_2$O

Acetamide 5a (Scheme 2). Treatment of 2b with acrylonitrile and NaH in DMF, followed by reduction with H$_2$ and Raney nickel in $Ac_2O$, as described above for the preparation of 4, gave the acetamide 5a.

Scheme 3

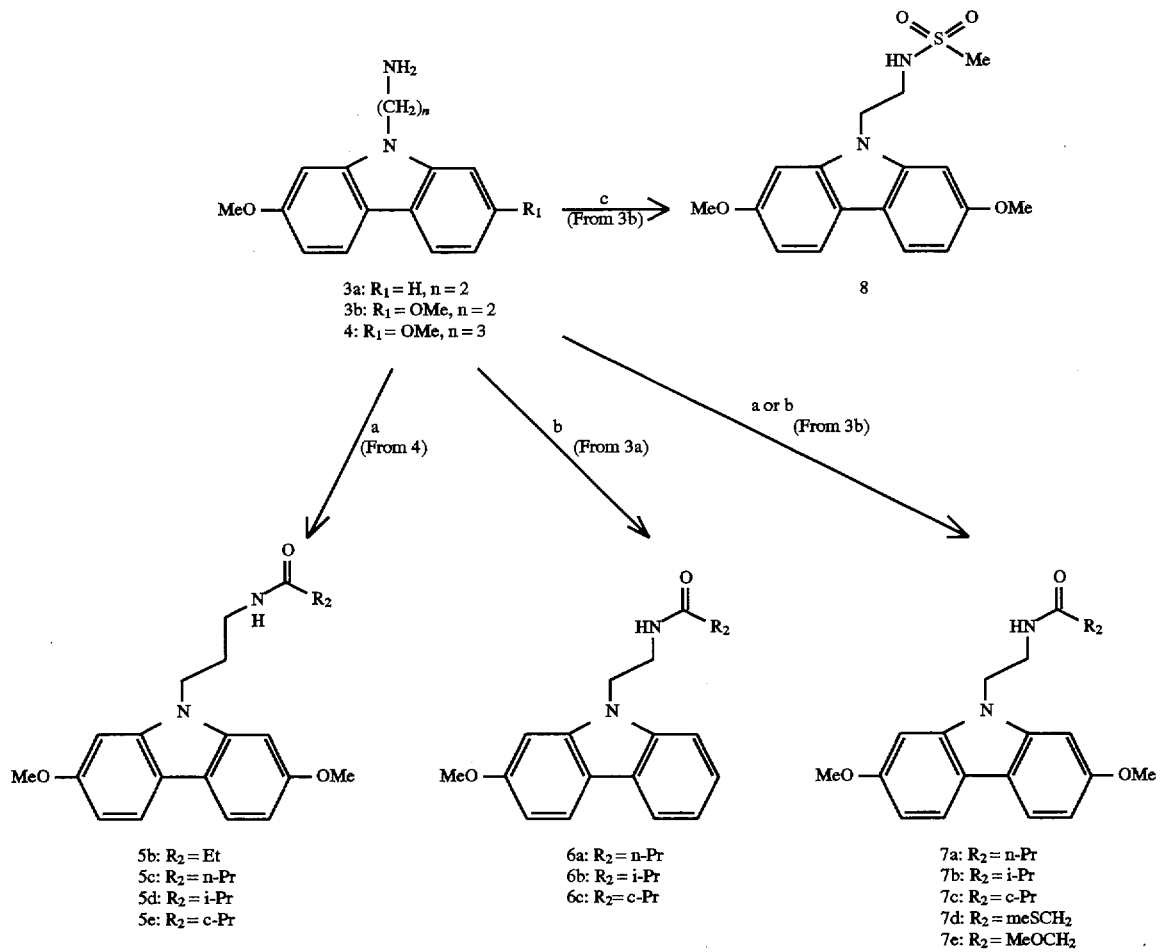

a: $R_2COCl$, $Et_3N$, $CH_2Cl_2$ (Method A).
b: $R_2CO_2H$, Ethyl 3-N,N-dimethylaminopropyl carbodiimide, $CH_2Cl_2$ (Method b).
c: MsCl, $Et_3N$, $CH_2Cl_2$.

Amide Derivatives 5, 6, 7, and 8 (Scheme 3). Amides 5b–e were prepared by acylation of 4 with the appropriate acid chlorides in the presence of $Et_3N$ and $CH_2C_{12}$ (Method A). Compounds 7e and 8 were prepared in a similar manner from amine 3b.

General Procedure for the Synthesis of Amides 5b–e, 7e, and 8: Method A.

The appropriate amine hydrochloride salt was taken up in $CH_2Cl_2$ and made basic with saturated $Na_2CO_3$. The organic extract was dried ($Na_2SO_4$), and the solvent was removed in vacuo to afford the free base. A solution of the free base (0.75 mmol), the appropriate acid chloride (1.0 mmol), and $Et_3N$ (0.14 mL, 1.0 mmol) in $CH_2Cl_2$ (10 mL) was stirred for 2 h, and then filtered through a Varian SCX sorbent cartridge, eluting with $CH_2Cl_2$ to $CH_2Cl_2$:MeOH 98:2. The solvent was removed in vacuo and the residue was triturated in ether and filtered to furnish the desired product.

Amides 6 and 7a–d were prepared via an alternative method by coupling the appropriate amines and carboxylic acids in the presence of ethyl 3-(N,N-dimethylamino)propyl carbodiimide (EDC) in $CH_2Cl_2$ (Method B).

General Procedure for the Preparation of Amides 6 and 7a–d: Method B.

The appropriate amine hydrochloride salt (3a or 3b) was taken up in $CH_2Cl_2$ and made basic with saturated $Na_2CO_3$.

The organic extract was dried ($Na_2SO_4$), and the solvent was removed in vacuo to give the free base as a colorless oil. A mixture of the free base (0.50 mmol), the appropriate carboxylic acid (0.80 mmol) and ethyl 3-(N,N-dimethylamino)propyl carbodiimide (EDC, 115 mg, 0.6 mmol) in $CH_2Cl_2$ (10 mL) was stirred for 3 h. The crude reaction mixture was filtered through a Varian SAX anion exchange sorbent cartridge (SAX sorbent, 2.0 g) containing additional Varian SCX cation exchange sorbent (2.0 g). The desired product was eluted with $CH_2Cl_2$:MeOH 98:2, the solvent was removed in vacuo, and the residue was dried in an Abderhalden pistol overnight at 82° C.

Scheme 4
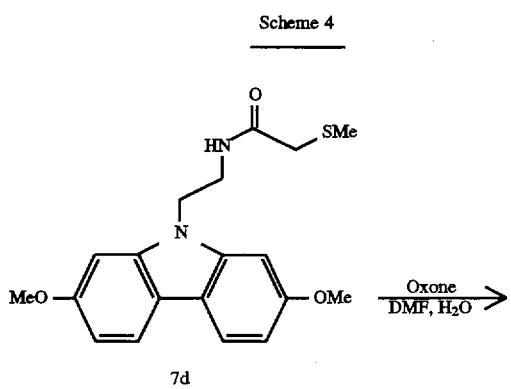
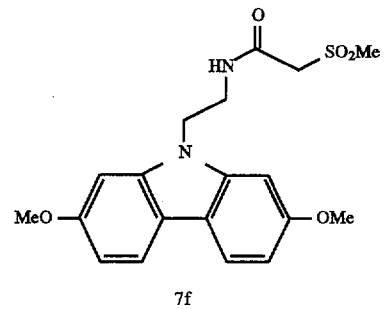
Amide 7f (Scheme 4). The methanesulfonylacetamide derivative 7f was prepared by oxidation of the methylthioacetamide 7d with Oxone in DMF/H$_2$O.
Scheme 5
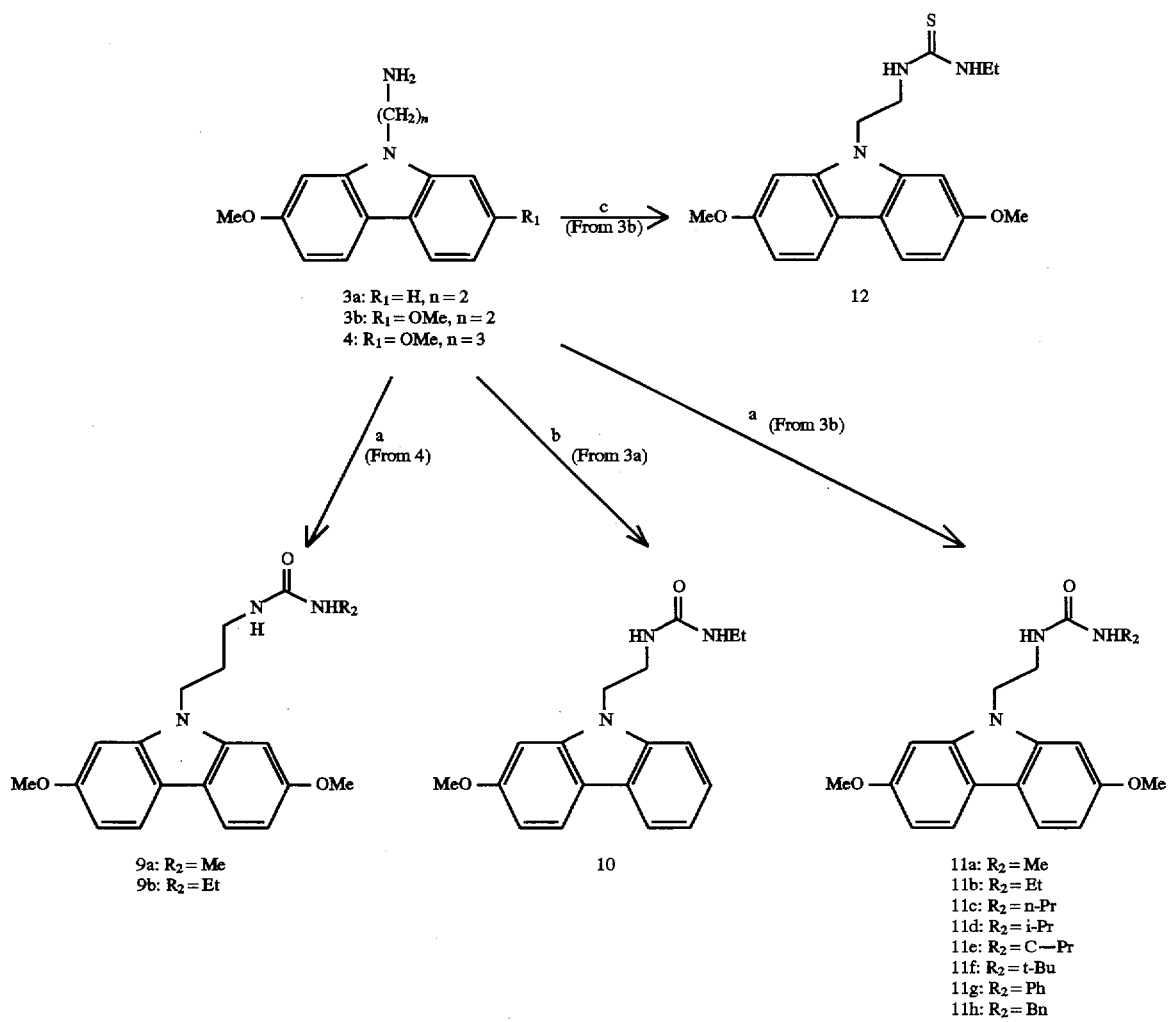
3a: R$_1$ = H, n = 2
3b: R$_1$ = OMe, n = 2
4: R$_1$ = OMe, n = 3
9a: R$_2$ = Me
9b: R$_2$ = Et
11a: R$_2$ = Me
11b: R$_2$ = Et
11c: R$_2$ = n-Pr
11d: R$_2$ = i-Pr
11e: R$_2$ = C—Pr
11f: R$_2$ = t-Bu
11g: R$_2$ = Ph
11h: R$_2$ = Bn
a: R$_2$NCO, CH$_2$Cl$_2$.
b: EtNCO, CH$_2$Cl$_2$
c: EtNCS, CH$_2$Cl$_2$.

Ureas 9, 10, 11, and 12 (Scheme 5). The ureas 9a–b were prepared from the amine 4 and the appropriate isocyanate in $CH_2Cl_2$. In a similar manner, ureas 10 and 11a–h were prepared from the appropriate isocyanates and the amines 3a and 3b, respectively. In addition, the thiourea 12 was prepared from 3b and ethyl isothiocyanate.

General Procedure for the Preparation of ureas 9, 10, 11, and thiourea 12.

A solution of the appropriate amine free base (0.75 mmol) and the appropriate isocyanate or isothiocyanate (1.5 mmol) in $CH_2Cl_2$ (10 mL) was stirred for 2 h. The solvent was then reduced under a stream of $N_2$, and a small amount of ether was added. The resulting precipitate was collected by filtration to furnish the desired product.

ADMINISTRATION

The compounds of the invention may be administered to patients in need of melatonergic treatment i.e., patients suffering from sleep disorders and the like, in a variety of ways. Thus, oral, transdermal, subcutaneous, intravenous, intramuscular, rectal, buccal, intranasal, and ocular routes can be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatibility, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate, mineral oil and the like. Mixtures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.9 to 90%, or other suitable amounts, of excipient(s).

Dosage levels will be dictated by the patient's needs and by the medical judgment of the treating physician. Generally, however, dosages of about 0.1 mg to about 10 mg per day, preferably about 1 mg to about 2 mg per day, are useful to treat sleep or circadian rhythm disorders.

While human patients are most preferred, the compounds of the invention may be used to treat other subjects, i.e., animals preferably mammals.

SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) are spectral characteristics refer to Chemical shifts ($\delta$) expressed as parts per million (ppm) versus tetramethylsilane (TMS) as reference standard. The relative area reported for the various shifts in the $^1H$ NMR spectral data corresponds to the number of hydrogen atoms of a particular functional type in the molecule. The nature of the shifts as to multiplicity is reported as a broad singlet (bs), singlet (s), multiplet (m), doublet (d), or triplet (t). Abbreviations employed are DMSO-$d_6$ (deuterodimethylsulfoxide), $CDCl_3$ (deuterochloroform) and are otherwise conventional. The infrared (IR) spectral descriptions include only absorption wave numbers ($cm^{-1}$) having functional group identification value. The IR determinations were employed using the compound neat as a film or by employing potassium bromide (KBr) as diluent. The elemental analyses are reported as percent by weight. Unless otherwise notes, all percentages recited herein are weight percents, based on total composition weight.

The following examples describe in detail the preparation of compounds of Formula I. It will be apparent to those skilled in the art that modifications, both of materials and methods, will allow preparation of other compounds disclosed herein. From the foregoing description and the following examples it is believed that one skilled in the art is able to use the invention to the fullest extent.

EXAMPLES

Examples 1–7 show the preparation of intermediates necessary for the preparation of various Formula I compounds.

Examples 8–34 show specific examples of various Formula I compounds.

Example 35 sets out the human $ML_{1a}$ binding assay used to test activity.

Example 1

4-Methoxy-2'-nitro-1,1'-biphenyl

Anhydrous THF (200 mL) was added to a 1.0 L 3-necked flask containing flame-dried magnesium turnings (9.72 g, 400 mg.atom) under $N_2$, followed by a small amount of $I_2$. A solution of 4-bromoanisole (25.0 mL, 200 mmol) in anhydrous THF (100 mL) was introduced portionwise with gradual heating at 65° C., and the resulting mixture heated at 65° C. for 2 h. The mixture was then cooled, and the supernatant was decanted. The residue was washed with THF, and the supernatant and wash were combined in an addition funnel. This solution was then added dropwise to a stirred solution of trimethyl borate (23.0 mL, 200 mmol) in anhydrous THF (150 mL) under $N_2$. Stirring was continued for 1 h, 5% $H_2SO_4$ (200 mL) was added, and the mixture was stirred for an additional 30 min. The resulting suspension was extracted with $Et_2O$, the organic extract was rinsed with brine, dried ($Na_2SO_4$), and the solvent was reduced in vacuo. A white precipitate was collected by filtration (4-methoxyphenylboronic acid, 22.5 g, 74% yield), and was further reacted without characterization.

A solution of 4-methoxyphenylboronic acid (11.0 g, 72 mmol) in 95% EtOH (100 mL) was added to a solution of $(Ph_3P)_4Pd$ (2.25 g, 2.0 mmol) and 1-bromo-2-nitrobenzene (13.0 g, 65 mmol) in benzene (300 mL). A solution of $Na_2CO_3$ (2M, 150 mL, 300 mmol) was added, and the resulting mixture was refluxed with vigorous stirring overnight. The reaction mixture was then cooled, 30% $H_2O_2$ (20 mL) was added, and stirring was continued for 1 h. The resulting mixture was extracted with $Et_2O$, the organic extract was rinsed with brine, dried ($Na_2SO_4$), and the solvent was removed in vacuo. The residue was taken up in CH$_2$Cl$_2$:hexane 1:3, filtered through silica gel, and the biphenyl was eluted with CH$_2$Cl$_2$:Hexane 1:1. The solvent was removed in vacuo to afford a yellow solid (15.5 g, quantitative yield): mp 48°–50° C.; [Jones, B.; Chapman, F., J. Chem. Soc. 1829–1832 (1952)] $^1$H NMR (CDCl$_3$) δ7.78 (d, 1H, J=8.4 Hz), 7.57 (t, 1H, J=7.8 Hz), 7.42 (m, 2H), 7.24 (d, 2H, J=9.0 Hz 6.94 (d, 2H, J=9.0 Hz), 3.83 (s, 3H); $^{13}$C NMR (CDCl$_3$) δ159.70, 149.42, 135.85, 132.13, 131.92, 129.49, 129.12, 127.72, 123.99, 114.22, 55.31. Anal. Calcd for C$_{13}$H$_{11}$NO$_3$: C, 68.11; H, 4.84; N, 6.11. Found: C, 68.42; H, 4.79; N, 5.83.

Example 2

4,4'-Dimethoxy-2-nitro-1,1'-biphenyl

4-Methoxyphenylboronic acid was reacted with 4-bromo-3-nitroanisole as described for 1a to furnish a yellow solid (90% yield): mp 122°–124° C.; [Lund, H. et al, Acta. Chem. Scand., 20, 1631–1644 (1966)] $^1$H NMR (CDCl$_3$) δ7.30 (m, 2H), 7.18 (d, 2H, J=9.0 Hz), 7.10 (d, 1H, J=8.4 Hz), 6.92 (d, 2H, J=9.0 Hz), 3.87 (s, 3H), 3.82 (s, 3H); $^{13}$C NMR (CDCl$_3$): δ159.37, 158.80, 149.69, 132.76, 129.43, 129.19, 128.21, 118.60, 114.12, 108.90, 55.89, 55.28. Anal. Calcd for C$_{14}$H$_{13}$NO$_4$: C, 64.86; H, 5.05; N, 5.40. Found: C, 64.77; H, 4.96; N, 5.24.

Example 3

2-Methoxy-9H-carbazole

A solution of 1a (14.7 g, 64.1 mmol) in triethyl phosphite (50 mL) was refluxed for 4 h, and then cooled to room temperature. The resulting precipitate was collected by filtration and rinsed with Et$_2$O. The filtrate was rinsed with 1N HCl (2×250 mL), and the resulting precipitate in the organic extract was collected by filtration and combined with the previously obtained precipitate to furnish a white solid (9.0 g, 71% yield): mp 223°–225° C.; [Cummins, J. A.; Tomlinson, M. L., J. Chem. Soc., 3475–7 (1955)] $^1$H NMR (DMSO-d$_6$) δ11.11 (s, 1H), 7.97 (d, 1H, J=8.4 Hz), 7.95 (d, 1H, J=8.4 Hz), 7.42 (d, 1H, J=7.8 Hz), 7.27 (t, 1H, J=8.1 Hz), 7.09 (t, 1H, J =7.8 Hz), 6.95 (s, 1H), 6.75 (d, 1H, J=8.4 Hz), 3.82 (s, 3H); $^{13}$C NMR (DMSO-d$_6$) δ158.49, 141.10, 139.72, 124.11, 122.66, 120.89, 119.24, 118.53, 116.17, 110.60, 107.69, 94.43, 55.24. Anal. Calcd for C$_{13}$H$_{11}$NO.0.1H$_2$O: C, 78.45; H, 5.67; N, 7.04. Found: C, 78.54; H, 5.87; N, 6.77.

Example 4

2,7-Dimethoxy-9H-Carbazole

This compound was synthesized from 1b by the procedure given for 2a. A white solid was obtained (78% yield): mp 272°–275° C.; [Raj, K. et al, Indian L Chem., Sect. B, 14B, 371–3 (1976)] $^1$H NMR (DMSO-d$_6$) δ10.97 (s, 1 H), 7.82 (d, 2H, J=8.4 Hz), 6.92 (s, 2H), 6.71 (d, 2H, J=8.4 Hz), 3.80 (s, 6H); $^{13}$C NMR (DMSO-d$_6$) δ157.55, 141.03, 119.93, 116.46, 107.32, 94.65, 55.22. Anal. Calcd for C$_{14}$H$_{13}$NO$_2$.0.1H$_2$O: C, 73.99; H, 5.77; N, 6.16. Found: C, 73.91; H, 5.70; N, 6.14.

Example 5

2-Methoxy-9H-Carbazole-9-ethanamine hydrochloride

A solution of NaH (60% mineral oil dispersion, 750 mg, 19 mmol) and 2a (3.8 g, 19 mmol) in anhydrous DMF (50 mL) was stirred for 30 min under N$_2$. Bromoacetonitrile (1.5 mL, 19 mmol) was then added, and stirring was continued for 30 min. The reaction was then quenched with saturated NH$_4$C$_1$, sufficient water was added to dissolve all solids, and the mixture was extracted with EtOAc. The organic extract was rinsed with water and brine, dried (Na$_2$SO$_4$), and the solvent was removed in vacuo to give a 60:40 mixture of 2a and the 9-cyanomethyl product, respectively, as determined by $^1$H NMR. The mixture was subsequently reduced without further purification or characterization.

The mixture of 2a and the 9-cyanomethyl product described above was taken up in 2-methoxyethanol (250 mL) containing 30% aq NH$_3$ (45 mL) and Raney nickel (Aldrich, analogous to Raney 28 or W-2), and was hydrogenated on a Parr hydrogenation apparatus at 50 psi for 1 h. The catalyst was then removed by filtration over Celite, and the filtrate was partitioned between H$_{2O}$ (500 mL) and CH$_2$Cl$_2$ (2×100 mL). The organic extracts were combined, dried (Na$_2$SO$_4$), and the solvent was reduced in vacuo, to give a solution of 2a and 3a in a small amount of 2-methoxyethanol. This solution was taken up in Et$_{2O}$ (100 mL), and the resulting precipitate (2a) was removed by filtration. The filtrate was acidified with HCl (4N solution in 1,4-dioxane, 2.0 mL, 8.0 mmol). The resulting precipitate was collected by filtration to afford a white solid (1.54 g, 29% yield): mp 270°–272° C.; $^1$H NMR (DMSO-d$_6$) δ8.40 (s, 3H), 8.02 (d, 1H, J=8.1 Hz), 7.99 (d, 1H, J=8.7 Hz), 7.64 (d, 1H, J=8.1 Hz), 7.35 (m, 2H), 7.17 (t, 1H, J=7.2 Hz), 6.81 (d, 1H, J=8.4 Hz), 4.66 (t, 2H, J=6.9 Hz), 3.90 (s, 3H), 3.18 (m, 2H); $^{13}$C NMR (DMSO-d$_6$) δ159.05, 141.55, 139.98, 124.44, 122.76, 121.10, 119.43, 119.28, 115.98, 108.89, 108.19, 93.50, 55.74, 39.91, 37.41; Anal. Calcd for C$_{15}$H$_{16}$N$_2$O.HCl: C, 65.10; H, 6.19; N, 10.12. Found: C, 65.02; H, 6.08; N, 9.93.

Example 6

2,7-Dimethoxy-9H-carbazole-9-ethanamine hydrochoride

This compound was prepared from 2b as described above for 3a to furnish a white solid (35% yield): mp 273°–275° C.; $^1$H NMR (DMSO-d$_6$) δ8.40 (s, 3H), 7.86 (d, 2H, J=8.4 Hz), 7.27 (s, 2H), 6.76 (d, 2H, J=8.7 Hz), 4.62 (t, 2H, J =6.9 Hz), 3.85 (s, 6H), 3.16 (m, 2H); $^{13}$C NMR (DMSO-d$_6$) δ158.03, 141.44, 120.12, 116.33, 107.80, 93.69, 55.68, 39.80, 37.38; Anal. Calcd for C$_{16}$H$_{18}$N$_2$O$_2$.HCl: C, 62.64; H, 6.24; N, 9.13. Found: C, 62.39; H, 6.33; N, 9.04.

Example 7

2,7-Dimethoxy-9H-carbazole-9-propanamine hydrochloride

A solution of 2b (8.0 g, 35 mmol) in anhydrous DMF (200 mL) was treated with NaH (60% mineral oil dispersion, 1.4 g, 35 mmol). The resulting mixture was stirred for 2 h under N$_2$, followed by dropwise addition of acrylonitrile (43 mL, 700 mmol). The reaction was stirred for an additional 3 h, and then quenched with saturated NH$_4$Cl . H$_2$O (400 mL) and EtOAc (400 mL) were added, and the mixture was shaken, filtered over Celite, and partitioned. The organic extract was rinsed with water (3×200 mL), followed by brine (200 mL), dried (Na$_2$SO$_4$), and the solvent was removed in vacuo. The residue was taken up in CH$_2$Cl$_2$, filtered, and the filtrate was passed through a plug of silica gel, eluting with CH$_2$Cl$_2$. The solvent was removed in vacuo, and the residue was recrystallized in EtOAc to furnish a white solid (3.9 g, 2,7-dimethoxy-9H-carbazole-9-propanenitrile, ca. 95% pure by $^1$H NMR, remainder 2b). The propanenitrile was not further purified or characterized. This material was taken up in Ac$_2$O (150 mL) containing Raney Nickel (Aldrich, analogous to Raney 28 or W-2), and was shaken in a Parr hydrogenation apparatus at 50 psi for 2 h. The catalyst was then removed by filtration over Celite, and the filtrate was carefully added to 10% NaOH (300 mL). The resulting mixture was refluxed for 1 h, then cooled, and the resulting acetamide was collected by filtration. This was subsequently hydrolyzed by refluxing overnight in a mixture of 20% NaOH (150 mL) and EtOH (150 mL). The resulting solution was cooled and extracted with $CH_2Cl_2$ (200 mL). The organic extract was dried ($Na_2SO_4$), and the solvent was reduced in vacuo to an ethanolic suspension (ca. 50 mL) and filtered. The solvent was removed in vacuo from the filtrate, the residue was taken up in $CH_2Cl_2$, and the resulting mixture was filtered. The filtrate was acidified with 1N HCl in ether (11.0 mL, 11.0 mmol). The resulting precipitate was collected by filtration to afford a white solid (2.40 g, 21% yield for 3 steps): mp 232°–235° C.; $^1$H NMR (DMSO-d$_6$) δ8.20 (br s, 3H), 7.86 (d, 2H, J=8.4 Hz), 7.20 (s, 2H), 6.75 (d, 2H, J=8.4 Hz), 4.45 (t, 2H, J=6.6 Hz), 3.86 (s, 6H), 2.83 (m, 2H), 2.05 (qu, 2H, J=6.6 Hz); $^{13}$C NMR (DMSO-d$_6$) δ157.94, 141.33, 120.09, 116.13, 107.34, 93.84, 55.63, 39.51, 36.61, 26.41. Anal. calcd for $C_{17}H_{20}N_2O_2 \cdot HCl$: C, 63.65; H, 6.60; N, 8.73. Found: C, 63.31; H, 6.58; N, 8.50.

Example 8

N-[3-(2,7-Dimethoxy-9H-carbazol-9-yl)propyl]acetamide

This compound was isolated as an intermediate in the synthesis of 4. A white solid was obtained (31% yield, in 2 steps from 2b): mp 120°–122° C.; $^1$H NMR (DMSO-d$_6$) δ8.01 (m, 1H), 7.86 (d, 2H, J=8.4 Hz), 7.07 (s, 2H), 6.74 (d, 2H, J=8.4 Hz), 4.32 (t, 2H, J=6.9 Hz), 3.84 (s, 6H), 3.07 (q,2H, J=5.7 Hz), 1.87 (m, 2H), 1.81 (s, 3H); $^{13}$C NMR (DMSO-d$_6$) δ169.19, 157.84, 141.38, 120.05, 116.11, 107.19, 93.59, 55.45, 39.91, 36.46, 28.26, 22.60. Anal. Calcd for $C_{19}H_{22}N_2O_3 \cdot 0.7H_2O$: C, 67.31; H, 6.96; N, 8.26. Found: C, 67.25; H, 6.57; N, 8.09.

Example 9

N-[3-(2,7-Dimethoxy-9H-carbazol-9-yl)propyl] propanamide

This compound was obtained as a white solid (95% yield): mp 150°–152° C.; $^1$H NMR (DMSO-d$_6$) δ7.86 (m, 3H), 7.06 (s, 2H), 6.75 (d, 2H, J=8.4 Hz), 4.31 (t, 2H, J=6.6 Hz), 3.84 (s, 6H), 3.08 (q, 2H, J=6.3 Hz), 2.07 (q, 2H, J=7.8 Hz), 1.87 (qu, 2H, J=6.9 Hz), 0.98 (t, 3H, J=7.5 Hz); $^{13}$C NMR (DMSO-d$_6$) δ172.88, 157.85, 141.38, 120.06, 116.12, 107.16, 93.59, 55.43, 39.91, 36.39, 28.55, 28.33, 9.99. Anal. Calcd for $C_{20}OH_{24}N_2O_3$: C, 70.57; H, 7.11; N, 8.23. Found: C, 70.52; H, 6.98; N, 8.12.

Example 10

N-[3-(2,7-Dimethoxy-9H-carbazol-9-yl)propyl]butanamide

This compound was obtained as a white solid (86% yield): mp 146°–147° C.; $^1$H NMR (DMSO-d$_6$) δ7.86 (m, 3H), 7.06 (s, 2H), 6.75 (d, 2H, J=8.4 Hz), 4.31 (t, 2H, J=6.9 Hz), 3.84 (s, 6H), 3.10 (q, 2H, J=6.0 Hz), 2.04 (t, 2H, J=7.2 Hz), 1.87 (qu, 2H, J=7.5 Hz), 1.51 (m, 2H), 0.84 (t, 3H, J=7.3 Hz);$^{13}$C NMR (DMSO-d$_6$) δ171.99, 157.86, 141.37, 120.06, 116.13, 107.15, 93.60, 55.44, 39.96, 37.41, 36.35, 28.39, 18.72, 13.67. Anal. Calcd for $C_{21}H_{26}N_2O_3 \cdot 0.2 H_2O$: C, 70.45; H, 7.43; N, 7.82. Found: C, 70.41; H, 7.34; N, 7.73.

Example 11

N-[3-(2,7-Dimethoxy-9H-carbazol-9-yl)propyl]-2-methylpropanamide

This compound was obtained as a white solid (80% yield): mp 145°–146° C.; $^1$H NMR (DMSO-d$_6$) δ7.86 (d, 2H, J=8.7 Hz), 7.83 (m, 1H), 7.05 (s, 2H), 6.74 (d, 2H, J=8.7 Hz), 4.30 (t, 2H, J=6.9 Hz), 3.84 (s, 6H), 3.09 (q, 2H, J=6.0 Hz), 2.34 (m, 1H), 1.86 (m, 2H), 0.98 (d, 6H, J=6.3 Hz); $^{13}$C NMR (DMSO-d$_6$) δ176.09, 157.85, 141.36, 120.07, 116.13, 107.14, 93.60, 55.45, 39.95, 36.33, 34.06, 28.37, 19.61. Anal. Calcd for $C_{21}H_{26}N_2O_3 \cdot 0.1H_2O$: C, 70.80; H, 7.41; N, 7.86. Found: C, 70.71; H, 7.53; N, 7.89.

Example 12

N-[3-(2,7-Dimethoxy-9H-carbazol-9-yl)propyl] Cyclopropanecarboxamide

This compound was obtained as a white solid (70% yield): mp 153°–155° C.; $^1$H NMR (DMSO-d$_6$) δ8.16 (m, 1H), 7.87 (d, 2H, J=8.4 Hz), 7.06 (s, 2H), 6.75 (d, 2H, J=8.4 Hz), 4.32 (t, 2H, J=6.9 Hz), 3.84 (s, 6H), 3.10 (q, 2H, J=6.0 Hz), 1.89 (qu, 2H, J=5.4 Hz), 1.53 (m, 1H), 0.61 (m, 4H); $^{13}$C NMR (DMSO-d$_6$) δ172.53, 157.85, 141.38, 120.06, 116.10, 107.21, 93.53, 55.43, 40.08, 36.60, 28.41, 13.59, 6.09. Anal. Calcd for $C_{21}{}^1H_{24}N_2O_3$: C, 71.57; H, 6.86; N, 7.95. Found: C, 71.26; H, 6.88; N, 7.79.

Example 13

N-[2-(2,7-Dimethoxy-9H-carbazol-9-yl)ethyl] methoxyacetamide

This compound was obtained as a white solid (100% yield): mp 136°–138° C.; $^1$H NMR (DMSO-d$_6$) δ7.99 (t, 1H, J=6.0 Hz), 7.85 (d, 2H, J=8.4 Hz), 7.10 (s, 2H), 6.74 (d, 2H, J=8.4 Hz), 4.37 (t, 2H, J=5.4 Hz), 3.84 (s,6H), 3.66 (s, 2H), 3.48 (q, 2H, J=6.0 Hz), 3.16 (s, 3H); $^{13}$C NMR (DMSO-d$_6$) δ169.52, 157.83, 141.57, 120.04, 116.13, 107.32, 93.43, 71.46, 58.53, 55.38, 41.31, 37.10. Anal. Calcd for $C_{19}H_{22}N_2O_4$: C, 66.65; H, 6.48; N, 8.18. Found: C, 65.68; H, 6.44; N, 8.02.

Example 14

N-[2-(2,7-Dimethoxy-9H-carbazol-9-yl)ethyl] methanesulfonamide

This compound was obtained as a white solid (88% yield): mp 163°–165° C.; $^1$H NMR (DMSO-d$_6$) δ7.86 (d, 2H, J=8.4 Hz), 7.28 (t, 1H, J=6.0 Hz), 7.13 (s, 2H), 6.76 (d, 2H, J=8.4 Hz), 4.39 (t, 2H, J=6.0 Hz), 3.85 (s, 6H), 3.33 (q, 2H, J=6.0 Hz), 2.73 (s, 3H); $^{13}$C NMR (DMSO-d$_6$) δ157.86, 141.53, 120.04, 116.17, 107.41, 93.78, 55.42, 42.84, 41.23, 37.13. Anal. Calcd for $C_{17}H_{20}N_2O_4S \cdot 0.3H_2O$: C, 57.71; H, 5.87; N, 7.92. Found: C, 57.85; H, 5.80; N, 7.72.

Example 15

N-[2-(2-Methoxy-9H-carbazol-9-yl)ethyl]butanamido

This compound was obtained as a white solid (88% yield): mp 140°–142° C.; $^1$H NMR (DMSO-d$_6$) δ7.95 (m, 3H), 7.49 (d, 1H, J=8.1 Hz), 7.33 (t, 1H, J=8.1 Hz), 7.14 (t, 1H, J=7.2 Hz), 7.11 (s, 1H), 6.78 (d, 1H, J=8.4 Hz), 4.39 (t, 2H, J=6.3 Hz), 3.86 (s, 3H), 3.43 (q, 2H, J=6.0 Hz), 1.90 (t, 2H, J=7.5 Hz), 1.41 (m, 2H), 0.73 (t, 3H, J=7.5 Hz); $^{13}$C NMR (DMSO-d$_6$) δ172.54, 158.78, 141.62, 140.24, 124.20, 122.43, 120.98, 119.32, 118.83, 115.84, 108.79, 107.65, 93.25, 55.41, 41.59, 37.72, 37.32, 18.33, 13.61. Anal. Calcd for $C_{19}H_{22}N_2O_2$: C, 73.52; H, 7.14; N, 9.03. Found: 73.35; H, 7.05; N, 8.83.

Example 16

N-[2-(2-methoxy-9H-carbazol-9-yl)ethyl]-2-methylpropanamide

This compound was obtained as a white solid (62% yield): mp 152°–154° C.; $^1$H NMR (DMSO-d$_6$) δ7.99 (m, 2H), 7.86 (t, 1H, J=5.4 Hz), 7.48 (d, 1H, J=8.1 Hz), 7.32 (t, 1H, J=8.1 Hz), 7.14 (t, 1H, J=7.2 Hz), 7.10 (s, 1H), 6.79 (d, 1H, J=8.7 Hz), 4.39 (t, 2H, J=6.3 Hz), 3.86 (s, 3H), 3.44 (q, 2H, J=6.0 Hz), 2.16 (m, 1H), 0.85 (d, 6H, J=6.9 Hz); $^{13}$C NMR (DMSO-$d_6$) δ176.53, 158.74, 141.64, 140.29, 124.17, 122.42, 120.97, 119.30, 118.82, 115.86, 108.89, 107.56, 93.40, 55.44, 41.55, 37.74, 34.04, 19.30. Anal. Calcd for $C_{19}H_{22}N_2O_2$: C, 73.52; H, 7.14; N, 9.03. Found: C, 73.36; H, 7.06; N, 8.79.

Example 17

N-[2-(2-Methoxy-9H-carbazol-9-yl)ethyl] cyclopropanecarboxamide

This compound was isolated as a white solid (85% yield): mp 135°–140° C.; $^1$H NMR (DMSO-$d_6$) δ8.22 (t, 1H, J=5.4 Hz), 8.00 (d, 1H, J=6.9 Hz), 7.98 (d, 1H, J=8.4 Hz), 7.47 (d, 1H, J=8.1 Hz), 7.33 (t, 1H, J=7.2 Hz), 7.14 (t, 1H, J=7.2 Hz), 7.08 (s, 1H), 6.79 (d, 1H, J=8.7 Hz), 4.39 (t, 2H, J=6.0 Hz), 3.86 (s, 3H), 3.44 (q, 2H, J=6.0 Hz), 1.38 (m, 1H), 0.64 (m, 2H), 0.58 (m, 2H); $^{13}$C NMR (DMSO-$d_6$) δ173.28, 158.80, 141.64, 140.25, 124.23, 122.42, 120.97, 119.30, 118.86, 115.85, 108.84, 107.70, 93.25, 55.41, 41.61, 38.13, 13.61, 6.14. Anal. Calcd for $C_{19}H_{20}N_2O_2$: C, 74.00; H, 6.54; N, 9.08. Found: C, 73.79; H, 6.53; N, 8.78.

Example 18

N-[2-(2,7-Dimethoxy-9H-carbazol-9-yl)ethyl]butanamide

This compound was obtained as a white solid (88% yield): mp 140°–142° C.; $^1$H NMR (DMSO-$d_6$) δ7.94 (t, 1H, J=5.7 Hz), 7.85 (d, 2H, J=8.4 Hz), 7.06 (s, 2H), 6.74 (d, 2H, J=8.4 Hz), 4.34 (t, 2H, J=6.0 Hz), 3.84 (s, 6H), 3.42 (q, 2H, J=6.0 Hz), 1.91 (t, 2H, J=7.5 Hz), 1.39 (m, 2H), 0.73 (t, 3H, J=7.2 Hz); $^{13}$C NMR (DMSO-$d_6$) δ172.49, 157.76, 141.57, 119.94, 116.11, 107.21, 93.46, 55.34, 41.48, 37.53, 37.32, 18.28, 13.54; Anal. Calcd for $C_{20}H_{24}N_2O_3$: C, 70.57; H, 7.11; N, 8.23. Found: C, 70.30; H, 7.11; N, 7.99.

Example 19

N-[2-(2,7-Dimethoxy-9H-carbazol-9-yl)ethyl]-2-methylpropanamide

This compound was obtained as a white solid (62% yield): mp 152°–154° C.; $^1$H NMR (DMSO-$d_6$) δ7.85 (m, 3H), 7.05 (s, 2H), 6.74 (d, 2H, J=8.4 Hz), 4.35 (t, 2H, J=6.0 Hz), 3.84 (s, 6H), 3.43 (q, 2H, J=6.0 Hz), 2.17 (m, 1H), 0.85 (d, 6H, J=6.6 Hz); $^{13}$C NMR (DMSO-$d_6$) δ176.51, 157.79, 141.66, 119.98, 116.19, 107.17, 93.68, 55.43, 41.52, 37.58, 34.07, 19.28; Anal. Calcd for $C_{20}H_{24}N_2O_3$ .0.2$H_2O$: C, 69.83; H, 7.15; N, 8.14. Found: C, 69.93; H, 7.04; N, 7.97.

Example 20

N-[2-(2,7-Dimethoxy-9H-carbazol-9-yl)ethyl] cyclopropanecarboxamide

This compound was obtained as a white solid (99% yield): mp 170°–172° C.; $^1$H NMR (DMSO-$d_6$) δ8.28 (t, 1H, J=5.7 Hz), 7.85 (d, 2H, J=8.4 Hz), 7.04 (s, 2H), 6.74 (d, 2H, J=8.4 Hz), 4.35 (t, 2H, J=6.0 Hz), 3.84 (s, 6H), 3.43 (q, 2H, J=6.0 Hz), 1.40 (m, 1H), 0.63 (m, 2H), 0.56 (m, 2H); $^{13}$C NMR (DMSO-$d_6$) δ173.24, 157.84, 141.64, 119.98, 116.16, 107.33, 93.52, 55.41, 41.66, 38.04, 13.62, 6.13. High resolution mass spectroscopy for MH$^+$=$C_{20}H_{23}N_2O_3$: Calcd, 339.1709; found, 339.1702; deviation, 2.1 ppm.

Example 21

N-[2-(2,7-Dimethoxy-9H-carbazol-9-yl)ethyl] methylthioacetamide

This compound was obtained as a white solid (72% yield): mp 128°–130° C.; $^1$H NMR (DMSO-$d_6$) δ8.16 (t, 1H, J=5.7 Hz), 7.85 (d, 2H, J=8.4 Hz), 7.10 (s, 2H), 6.75 (d, 2H, J=8.4 Hz), 4.37 (d, 2H, J=6.0 Hz), 3.85 (s, 6H), 3.47 (q, 2H, J=6.0 Hz), 2.97 (s, 2H), 1.89 (s, 3H); $^{13}$C NMR (DMSO-$d_6$) δ169.30, 157.87, 141.60, 120.06, 116.17, 107.40, 93.50, 55.44, 41.41, 37.89, 36.63, 15.36. Anal. Calcd for $C_{19}H_{22}N_2O_3S$: C, 63.66; H, 6.19; N, 7.82. Found: C, 63.62; H, 6.14; N, 7.63.

Example 22

N-[2-(2,7Dimethoxy-9H-carbazol-9-yl)ethyl]-2-(methanesulfonyl)acetamide

A solution of 7d (200 mg, 0.55 mmol) in DMF (20 mL) was combined with a solution of Oxone (Aldrich, 600 mg, 1.0 mmol) in $H_2O$ (5 mL), and the resulting mixture was stirred 48 h. Water was then added, and the resulting precipitate was collected by filtration and rinsed with water. The solid was taken up in a minimum of $CH_2Cl_2$, the volume was reduced, and ether was added. The resulting precipitate was collected by filtration to afford a light gray solid (140 mg, 65% yield): mp 175°–177° C.; $^1$H NMR (DMSO-$d_6$) δ8.57 (t, 1H, J=5.7 Hz), 7.86 (d, 2H, J=8.4 Hz), 7.10 (s, 2H), 6.76 (d, 2H, J=8.4 Hz), 4.35 (t, 2H, J=6.3 Hz), 3.99 (s, 2H), 3.85 (s,6H), 3.51 (q, 2H, J=6.0 Hz), 3.07 (s, 3H); $^{13}$C NMR (DMSO-$d_6$) δ162.69, 157.89, 141.47, 120.07, 116.18, 107.50, 93.47, 59.37, 55.43, 41.49, 41.42, 37.35. Anal. Calcd for $C_{19}H_{22}N_2O_5S$: C, 58.45; H, 5.68; N, 7.17. Found: C, 58.30; H, 5.72; N, 7.13.

Example 23

N-[3-(2,7-Dimethoxy-9H-carbazol-9-yl)propyl]-N'-methylurea

This compound was obtained as a white solid (78% yield): mp 272°–274° C.; $^1$H NMR (DMSO-$d_6$) δ7.86 (d, 2H, J=8.4 Hz), 7.04 (s, 2H), 6.74 (d, 2H, J=8.4 Hz), 6.07 (t, 1H, J=5.4 Hz), 5.76 (s, 1H), 4.29 (t, 2H, J=6.9 Hz), 3.84 (s, 6H), 3.02 (q, 2H, J=6.0 Hz), 2.52 (d, 3H, J=3.6 Hz), 1.84 (qu, 2H, J=6.9 Hz); $^{13}$C NMR (DMSO-$d_6$) δ158.89, 157.91, 141.46, 120.12, 116.16, 107.27, 93.55, 55.47, 39.88, 37.33, 29.22, 26.49. Anal. Calcd for $C_{19}H_{23}N_3O_3$ .0.3$H_2O$: C, 65.80; H, 6.86; N, 12.12. Found: C, 65.78; H, 6.62; N, 11.97.

Example 24

N-Ethyl-N'-[3-(2,7-dimethoxy-9H-carbazol-9-yl)propyl]urea

This compound was obtained as a white solid (65% yield): mp 268°–270° C.; $^1$H NMR (DMSO-$d_6$) δ7.86 (d, 2H, J=8.4 Hz), 7.04 (s, 2H), 6.74 (d, 2H, J=8.4 Hz), 6.02 (t, 1H, J=5.4 Hz), 5.84 (t, 1H, J=5.4 Hz), 4.29 (t, 2H, J=7.2 Hz), 3.84 (s, 6H), 3.01 (m, 4H), 1.84 (qu, 2H, J=6.9 Hz), 0.96 (t, 3H, J=6.9 Hz); $^{13}$C NMR (DMSO-$d_6$) δ158.13, 157.84, 141.38, 120.04, 116.10, 107.19, 93.50, 55.41, 39.80, 37.16, 34.10, 29.18, 15.71. Anal. Calcd for $C_{20}H_{25}N_3O_3$ .0.5$H_2O$: C, 65.91; H, 7.19; N, 11.53. Found: C, 65.95; H, 6.89; N, 11.46.

Example 25

N-Ethyl-N'-[2-(2-methoxy-9H-carbazol-9-yl)ethyl]urea

This compound was obtained as a white solid (76% yield): mp 170°–172° C.; $^1$H NMR (DMSO-$d_6$) δ8.00 (d, 1H, J=7.2 Hz), 7.97 (d, 1H, J=8.4 Hz), 7.52 (d, 1H, J=8.4 Hz), 7.32 (t, 1H, J=6.9 Hz), 7.13 (m, 2H), 6.78 (d, 1H, J=8.4 Hz), 5.89 (m, 2H), 4.35 (d, 2H, J=6.6 Hz), 3.86 (s, 3H), 3.36 (m, 2H), 3.10 (qu, 2H, J=6.9 Hz), 0.95 (t, 3H, J=7.2 Hz); $^{13}$C NMR (DMSO-$d_6$) δ158.78, 158.17, 141.71, 140.26, 124.22, 122.37, 120.92, 119.27, 118.78, 115.75, 108.89, 107.65, 93.29, 55.35, 42.47, 38.50, 34.07, 15.68. Anal. Calcd for $C_{18}H_{21}N_3O_2$: C, 69.43; H, 6.80; N, 13.49. Found: C, 69.20; H, 6.80; N, 13.26.

Example 26

N-[2- (2,7-Dimethoxy-9H -carbazol-9-yl)ethyl]-N'-methylurea

This compound was obtained as a white solid (76% yield): mp 205°–206° C., $^1$H NMR (DMSO-$d_6$) δ7.85 (d, 2H, J=8.1 Hz), 7.08 (s, 2H), 6.74 (d, 2H, J=8.4 Hz), 6.00 (t, 1H, J=5.7 Hz), 5.83 (q, 1H, J=4.5 Hz), 4.32 (t, 2H, J=6.3 Hz), 3.84 (s, 6H), 3.34 (t, 2H, J=6.0 Hz), 2.54 (d, 3H, J=4.8 Hz); $^{13}$C NMR (DMSO-$d_6$) δ158.91, 157.81, 141.68, 119.95, 116.05, 107.35, 93.43, 55.32, 42.38, 38.55, 26.37. Anal. Calcd for $C_{18}H_{21}N_3O_3$: C, 66.04; H, 6.47; N, 12.84. Found: C, 65.87; H, 6.47; N, 12.88.

Example 27

N-Ethyl-N'[2-(2,7-dimethoxy -9H-carbazol-9-ethyl]urea

This compound was obtained as a white solid (99% yield): mp 198°–202° C.; $^1$H NMR (DMSO-$d_6$) δ7.85 (d, 2H, J=8.7 Hz), 7.07 (s, 2H), 6.74 (d, 2H, J=8.4 Hz), 5.90 (m, 2H), 4.31 (t, 2H, J=6.0 Hz), 3.84 (s, 6H), 3.35 (m, 2H), 3.00 (q, 2H, J=6.9 Hz), 0.94 (t, 3H, J=7.2 Hz); $^{13}$C NMR (DMSO-$d_6$) δ158.20, 157.83, 141.70, 119.94, 116.09, 107.28, 93.53, 55.34, 42.45, 38.48, 34.08, 15.62. Anal. Calcd for $C_{19}H_{23}N_3O_3$.0.5$H_2O$: C, 65.13; H, 6.90; N, 11.99. Found: C, 65.46; H, 6.64; N, 11.76.

Example 28

N-[2-(2,7-Dimethoxy -9H-carbazol-9-yl)ethyl]-N'-propylurea

This compound was obtained as a white solid (90% yield): mp 214°–215° C.; $^1$H NMR (DMSO-$d_6$) δ7.85 (d, 2H, J=8.4 Hz), 7.08 (s, 2H), 6.74 (d, 2H,J=8.4 Hz), 5.90 (m, 2H), 4.31 (t, 2H, J=5.7 Hz), 3.84 (s, 6H), 3.36 (m, 2H), 2.93 (q, 2H, J=6.6 Hz), 1.32 (m, 2H), 0.79 (t, 3H, J=7.5 Hz); $^{13}$C NMR (DMSO-$d_6$) δ158.29, 157.82, 141.69, 119.93, 116.08, 107.24, 93.54, 55.33, 42.46, 41.14, 38.45, 23.17, 11.35. Anal. Calcd for $C_{20}H_{25}N_3O_3$.0.2$H_2O$: C, 66.91; H, 7.13; N, 11.70. Found: C, 67.08; H, 6.93; N, 11.37.

Example 29

N-[2-(2,7-Dimethoxy-9H-carbazol-9-yl)ethyl]-N'-methylethyl)urea

This compound was obtained as a white solid (75% yield): mp 232°–233° C.; $^1$H NMR (DMSO-$d_6$) δ7.85 (d, 2H, J=8.4 Hz), 7.08 (s, 2H), 6.74 (d, 2H, J=8.4 Hz), 5.78 (m, 2H), 4.31 (t, 2H, J=6.3 Hz), 3.84 (s, 6H), 3.67 (m, 1H),3.36 (m, 2H), 0.98 (d, 6H, J=6.6 Hz); $^{13}$C NMR (DMSO-$d_6$) δ157.82, 157.62, 141.69, 119.93, 116.10, 107.19, 93.61, 55.35, 42.50, 48.40, 40.88, 23.23. Anal. Calcd for $C_{20}H_{25}N_3O_3$: C, 67.58; H, 7.09; N, 11.82. Found: C, 67.46; H, 7.13; N, 11.94.

Example 30

N-Cyclopropyl-N'-[2-(2,7-dimethoxy-9H-carbazol-9-yl)ethyl]urea (11e, BMS-1994534)

A solution of cyclopropyl isocyanate in o-dichlorobenzene was prepared according to the method described by Pilgram [Pilgram, K. H., U.S. Pat. No. 4,299, 778 (1981)]. The desired compound was then prepared according to the general procedure for urea derivatives to afford a white solid (49% yield): mp 182°–184° C.; $^1$H NMR (DMSO-$d_6$) δ7.85 (d, 2H, J=8.4 Hz), 7.09 (s, 2H), 6.74 (d, 2H, J=8.4 Hz), 6.29 (s, 1H), 6.04 (m, 1H), 4.34 (t, 2H, J=6.0Hz), 3.84 (s, 6H), 3.37 (q, 2H, J=6.0 Hz), 2.28 (m, 1H), 0.47 (m, 2H), 0.20 (m, 2H); $^{13}$C NMR (DMSO-$d_6$) δ158.98, 157.81, 141.70, 119.96, 116.07, 107.28, 93.53, 55.37, 42.21, 38.46, 22.21, 6.50. Anal. Calcd for $C_{20}H_{23}N_3O_3$.0.7$H_2O$: C, 65.63; H, 6.72; N, 11.48. Found: C, 65.49; H, 6.33; N, 11.35.

Example 31

N-[2-(2,7-Dimethoxy-9H-carbazol-9-yl )ethyl]-N'-(1,1-dimethylethyl)urea

This compound was obtained as a white solid (67% yield): mp 239°–240° C.; $^1$H NMR (DMSO-$d_6$) δ7.85 (d, 2H, J=8.4 Hz), 7.08 (s, 2H), 6.75 (d, 2H, J=8.4 Hz), 5.71 (m, 2H), 4.28 (t, 2H, J=6.0 Hz), 3.85 (s, 6H), 3.34 (m, 2H),1.20 (s, 9H); $^{13}$C NMR (DMSO-$d_6$) δ157.84, 157.57, 141.69, 119.92, 116.15, 107.12, 93.81, 55.40, 49.04, 42.85, 38.17, 29.30. Anal. Calcd for $C_{21}H_{27}N_3O_3$.0.1$H_2O$: C, 67.94; H, 7.39; N, 11.32. Found: C, 67.98; H, 7.34; N, 10.93.

Example 32

N-[2-(2,7-Dimethoxy-9H-carbazol-9-yl)ethyl]-N'-phenylurea

This compound was obtained as a white solid (92% yield): mp 214°–215° C.; $^1$H NMR (DMSO-$d_6$) δ8.52 (s, 1H), 7.86 (d, 2H, J=8.4 Hz), 7.39 (d, 2H, J=8.4 Hz), 7.22 (t, 2H, J=8.1 Hz), 7.10 (s, 2H), 6.90 (t, 1H, J=7.2 Hz),6.74(d, 2H, J=8.4 Hz), 6.19 (t, 1H, J=6.0 Hz), 4.41 (t, 2H, J=6.0 Hz), 3.76 (s, 6H), 3.47 (m, 2H); $^{13}$C NMR (DMSO-$d_6$)δ157.84, 155.62, 141.68, 140.35, 128.65, 121.20, 120.00, 117.80, 116.10, 107.47, 93.41, 55.24, 42.12, 38.46. Anal. Calcd for $C_{23}H_{23}N_3O_3$.0.4$H_2O$: C, 69.65; H, 6.05; N, 10.59. Found: C, 69.72; H, 5.93; N, 10.61.

Example 33

N-[2-(2,7-Dimethoxy-9H-carbazol-9-yl)ethyl]-N'-(phenylmethyl)urea

This compound was obtained as a white solid (84% yield): mp 208°–210° C.; $^1$H NMR (DMSO-$d_6$) δ7.87 (d, 2H, J=8.4 Hz), 7.28 (m, 2H), 7.20 (m, 3H), 7.11 (s, 2H), 6.76 (d, 2H, J=8.4 Hz), 6.44 (t, 1H, J=6.0 Hz), 6.06 (t,1H, J=5.7 Hz), 4.34 (t, 2H, J=6.0 Hz), 4.22 (d, 2H, J=5.7 Hz), 3.83 (s, 6H),3.14(q,2H, J=5.7 Hz); $^{13}$C NMR (DMSO-$d_6$) δ158.26, 157.84, 141.70, 140.73, 128.20, 127.00, 126.54, 119.96, 116.11, 107.27, 93.56, 55.35, 42.91, 42.53, 38.52. Anal. Calcd for $C_{24}H_{25}N_3O_3$: C, 71.44; H, 6.25; N, 10.41. Found: C, 71.20; H, 6.20; N, 10.19.

Example 34

N-Ethyl-N'-[2-(2,7-dimethoxy-9H-carbazol-9-yl)ethyl] thiourea

This compound was obtained as a white solid (82% yield): mp 187°–189° C.; $^1$H NMR (CDCl$_3$)δ7.77 (d, 2H, J=8.4 Hz), 6.91 (s, 2H), 6.78 (d, 2H, J=8.4 Hz), 5.72 (br m, 1H), 5.27 (br m, 1H), 4.52 (t, 2H, J=5.4 Hz), 3.96 (q, 2H, J=5.4 Hz), 3.88 (s, 6H), 2.84 (br m, 2H), 0.95 (t, 3H, J=7.2 Hz); $^{13}$C NMR (CDCl$_3$) δ158.35, 141.82, 120.19, 116.76, 107.84, 93.15, 55.74, 43.45, 41.58, 13.66. Anal. Calcd for C$_{19}$H$_{23}$N$_3$O$_2$S: C, 63.84; H, 6.48; N, 11.75. Found: C, 63.69; H, 6.42; N, 11.53.

The following table lists compounds prepared using procedures discussed above. The melting points of these compounds are also given.

TABLE 1

Melting Points of Selected Compounds

| Example | Compound | Melting Point (°C.) |
|---|---|---|
| 8 | N-[3-(2,7-Dimethoxy-9H-carbazol-9-yl)propyl]acetamide | 120–122 |
| 9 | N-[3-(2,7-Dimethoxy-9H-carbazol-9-yl)propyl]propanamide | 150–152 |
| 10 | N-[3-(2,7-Dimethoxy-9H-carbazol-9-yl)propyl]butanamide | 146–147 |
| 11 | N-[3-(2,7-Dimethoxy-9H-carbazol-9-yl)propyl]-2-methylpropanamide | 145–146 |
| 12 | N-[3-(2,7-Dimethoxy-9H-carbazol-9-yl)propyl]cyclopropanecarboxamide | 153–155 |
| 13 | N-[2-(2,7-Dimethoxy-9H-carbazol-9-yl)ethyl]methoxyacetamide | 136–138 |
| 14 | N-[2-(2,7-Dimethoxy-9H-carbazol-9-yl)ethyl]methanesulfonamide | 163–165 |
| 15 | N-[2-(2-Methoxy-9H-carbazol-9-yl)ethyl]butanamide | 140–142 |
| 16 | N-[2-(2-methoxy-9H-carbazol-9-yl)ethyl]-2-methylpropanamide | 152–154 |
| 17 | N-[2-(2-Methoxy-9H-carbazol-9-yl)ethyl]cyclopropanecarboxamide | 135–140 |
| 18 | N-[2-(2,7-Dimethoxy-9H-carbazol-9-yl)ethyl]butanamide | 140–142 |
| 19 | N-[2-(2,7-Dimethoxy-9H-carbazol-9-yl)ethyl]-2-methylpropanamide | 152–154 |
| 20 | N-[2-(2,7-Dimethoxy-9H-carbazol-9-yl)ethyl]cyclopropanecarboxamide | 170–172 |
| 21 | N-[2-(2,7-Dimethoxy-9H-carbazol-9-yl)ethyl]methylthioacetamide | 128–130 |
| 22 | N-[2-(2,7-Dimethoxy-9H-carbazol-9-yl)ethyl]-2-(methanesulfonyl)acetamide | 175–177 |
| 23 | N-[3-(2,7-Dimethoxy-9H-carbazol-9-yl)propyl]-N'-methylurea | 272–274 |
| 24 | N-Ethyl-N'-[3-(2,7-dimethoxy-9H-carbazol-9-yl)propyl]urea | 268–270 |
| 25 | N-Ethyl-N'-[2-(2-methoxy-9H-carbazol-9-yl)ethyl]urea | 170–172 |
| 26 | N-[2-(2,7-Dimethoxy-9H-carbazol-9-yl)ethyl]-N'-methylurea | 205–206 |
| 27 | N-Ethyl-N'-[2-(2,7-dimethoxy-9H-carbazol-9-yl)ethyl]urea | 198–202 |
| 28 | N-[2-(2,7-Dimethoxy-9H-carbazol-9-yl)ethyl]-N'-propylurea | 214–215 |
| 29 | N-[2-(2,7-Dimethoxy-9H-carbazol-9-yl)ethyl]-N'-(methylethyl)urea | 232–233 |
| 30 | N-Cyclopropyl-N'-[2-(2,7-dimethoxy-9H-carbazol-9-yl)ethyl]urea | 182–184 |
| 31 | N-[2-(2,7-Dimethoxy-9H-carbazol-9-yl)ethyl]-N'-(1,1-dimethylethyl)urea | 239–240 |
| 32 | N-[2-(2,7-Dimethoxy-9H-carbazol-9-yl)ethyl]-N'-phenylurea | 214–215 |
| 33 | N-[2-(2,7-Dimethoxy-9H-carbazol-9-yl)ethyl]-N'-(phenylmethyl)urea | 208–210 |
| 34 | N-Ethyl-N'-[2-(2,7-dimethoxy-9H-carbazol-9-yl)ethyl]thiourea | 187–189 |

Example 35

Measurement of Melatonergic Binding

1. Reagents
   (a) 50 mM Tris buffer containing 12.5mM MgCl$_2$ and 2mM EDTA (pH 7.4 at 37° C.).
   (b) Wash buffer: 20mM Tris base containing 2mM MgCl$_2$ (pH 7.4 at room temperature).
   (c) 6-Chloromelatonin (10$^{-5}$M final concn.).
   (d) 2-[$^{125}$I]-iodomelatonin (100 pM final concn.). Source: NEN 2. Membrane preparation. The cDNA (human ML$_{1A}$) was introduced into COS-1 cells by the DEAE-dextran method. Three days later, the media was removed, the plates washed with phosphate buffered saline, the cells removed using Hank's balanced salt solution and pelleted. The supernatant was discarded and the pellets frozen. For preparing membrane homogenates, pellets are thawed on ice, and resuspended in TME buffer, Tris base, MgCl$_2$, EDTA (pH 7.4 at 37° C.), supplemented with aprotinin, leupeptin, and phenylmethlysulfonylfluoride. The cells were then homogenized using a dounce homogenizer, and centrifuged. The resulting pellet was resuspended with a dounce homogenizer in TME and frozen. On the day of assay, the small aliquot was thawed on ice and resuspended in TME buffer.

3. Incubation: 37° C. for 1 hour. Reaction is terminated by filtration.

4. Activity: Compounds with an IC$_{50}$ value less than 500 nM are termed active.

The procedure was based on that disclosed in: Reppert, S. M., Weaver, D. R., and Ebisawa, R. (1994), Neuron, 13, 1177–1185 (1994).

The following table sets forth selected Formula I compounds and IC$_{50}$ (nM) activity data which demonstrates their usefulness.

TABLE II

Binding Data of Selected Compounds

| Example No. | ML$_{1a}$ binding* |
|---|---|
| 8 | +++ |
| 9 | +++ |
| 10 | +++ |
| 11 | ++ |
| 15 | +++ |
| 17 | ++ |
| 18 | ++ |
| 19 | ++ |
| 20 | +++ |
| 21 | +++ |
| 22 | + |
| 26 | +++ |
| 27 | +++ |

*ML$_{1a}$ human binding.
+++ = 0–100 nM;
++ = 100–250 nM;
+ = 250 nM or more.

Reasonable variations, such as those which would occur to one having ordinary skill in the art, can be made herein without departing from the scope of the invention.

We claim:

1. A compound of Formula I or a pharmaceutically acceptable salt thereof:

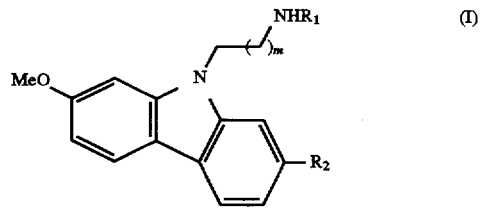

(I)

wherein:

R$_1$ is C(O)R$_3$, C(S)R$_3$, or SO$_2$R$_4$;

$R_2$ is H or $C_{1-6}$ alkoxy;

$R_3$ is $C_{1-6}$ alkyl, $C_{3-6}$ cycloalkyl, $(CH_2)_nSR_4$, $(CH_2)_nOR_4$, $(CH_2)SO_2R_4$, or $NHR_4$;

$R_4$ is $C_{1-4}$ alkyl; and m is 1 or 2; and n is 1 to 4.

2. The compound of claim 1 wherein $R_1$ is C(O)alkyl, C(O)cycloalkyl, C(S)NHalkyl, C(O)CH$_2$Salkyl, C(O)CH$_2$Oalkyl or C(O)NHalkyl; $R_2$ is hydrogen or a methoxy group; m is 1; and n is 1.

3. The compound of claim 2 selected from the group consisting of:

N-[2-(2-Methoxy-9H-carbazol-9-yl)ethyl]butanamide;

N-[2-(2-Methoxy-9H-carbazol-9-yl)ethyl] cyclopropanecarboxamide;

N-[2-(2,7-Dimethoxy-9H-carbazol-9-yl)ethyl] butanamide;

N-[2-(2,7-Dimethoxy-9H-carbazol-9-yl)ethyl]-2-methylpropanamide;

N-[2-(2,7-Dimethoxy-9H-carbazol-9-yl)ethyl] cyclopropanecarboxamide;

N-[2-(2,7-Dimethoxy-9H-carbazol-9-yl)ethyl] methylthioacetamide;

N-[2-(2,7-Dimethoxy-9H-carbazol-9-yl)ethyl] methoxyacetamide;

N-[2-(2,7-Dimethoxy-9H-carbazol-9-yl)ethyl]-N'-methylurea; and

N-Ethyl-N'-[2-(2,7-dimethoxy-9H-carbazol-9-yl)ethyl] urea.

4. N-[2-(2,7-Dimethoxy-9H-carbazol-9-yl)ethyl] methylthioacetamide.

5. N-Ethyl-N'-[2-(2,7-dimethoxy-9H-carbazol-9-yl)ethyl] urea.

6. The compound of claim 1 wherein $R_1$ is C(O)alkyl or C(O)cycloalkyl; $R_2$ is methoxy; m is 2; and n is 1.

7. The compound of claim 6 selected from the group consisting of:

N-[3-(2,7-Dimethoxy-9H-carbazol-9-yl)propyl] acetamide;

N-[3-(2,7-Dimethoxy-9H-carbazol-9-yl)propyl] propanamide;

N-[3-(2,7-Dimethoxy-9H-carbazol-9-yl)propyl] butanamide;

N-[3-(2,7-Dimethoxy-9H-carbazol-9-yl)propyl]-2-methylpropanamide; and

N-[3-(2,7-Dimethoxy-9H-carbazol-9-yl)propyl] cyclopropanecarboxamide.

8. N-[3-(2,7-Dimethoxy-9H-carbazol-9-yl)propyl] butanamide.

9. A method of treating a sleep disorder in a mammal in need of such treatment comprising administering to said mammal an effective amount of a compound of claim 1.

10. A pharmaceutical composition for treating sleep disorders comprising an effective amount of a compound of claim 1 and a suitable amount of a pharmaceutically acceptable carrier.

* * * * *